United States Patent [19]

Mandel et al.

[11] 4,034,850
[45] July 12, 1977

[54] PACKAGE FOR DOUBLE-ARMED SUTURES WITH SELF-CENTERING PLEDGETS

[75] Inventors: Harvey B. Mandel, North Brunswick; Michael Schuler, Piscataway, both of N.J.

[73] Assignee: Ethicon, Inc., Somerville, N.J.

[21] Appl. No.: 665,356

[22] Filed: Mar. 10, 1976

[51] Int. Cl.² .................................. A61L 17/02
[52] U.S. Cl. ............................. 206/63.3; 128/339; 206/227; 206/370; 206/382
[58] Field of Search .......... 223/99; 128/335.5, 335, 128/339; 206/63.3, 227, 388, 363, 370, 380, 382, 383, 484, 495

[56] References Cited

U.S. PATENT DOCUMENTS

| 2,199,025 | 4/1940 | Conn ................... | 128/335 |
| 2,591,063 | 4/1952 | Goldberg ................ | 128/339 |
| 2,948,999 | 8/1960 | Schlayer et al. ......... | 206/63.3 |
| 3,062,372 | 11/1962 | Egler et al. ............ | 206/63.3 |
| 3,180,487 | 4/1965 | Uddenborg .............. | 206/227 |
| 3,206,018 | 9/1965 | Lewis et al. ............ | 206/63.3 |
| 3,759,376 | 9/1973 | Lisowski ................ | 206/63.3 |
| 3,779,375 | 12/1973 | Foster .................. | 206/476 |
| 3,857,484 | 12/1974 | Thyen ................... | 206/63.3 |
| 3,910,281 | 10/1975 | Kletschka et al. ........ | 128/335 |
| 3,939,969 | 2/1976 | Miller et al. ........... | 206/63.3 |

FOREIGN PATENT DOCUMENTS

| 1,195,012 | 11/1959 | France .................. | 150/11 |
| 866,251 | 3/1961 | United Kingdom .......... | 206/63.3 |

*Primary Examiner*—George E. Lowrance
*Assistant Examiner*—Bruce H. Bernstein
*Attorney, Agent, or Firm*—Wayne R. Eberhardt

[57] ABSTRACT

A package for double-armed sutures equipped with a pledget and means for centering the pledget on the suture during removal of the suture from the package. The package comprises a double-armed suture in a storage compartment with the armed ends of the suture extending out of the compartment, a pledget slidably affixed to the suture strand approximate to one needle, and pledget centering means intermediate the pledget and said needle. Preferred pledget centering means comprise an integral passageway in the package material for the double suture strand and a barrier associated with said passageway which restrains the pledget as the suture is withdrawn from the package through the passageway, whereby the pledget is slidably displaced along the suture until the total length of the suture is withdrawn and the suture and pledget are released from the package.

23 Claims, 10 Drawing Figures

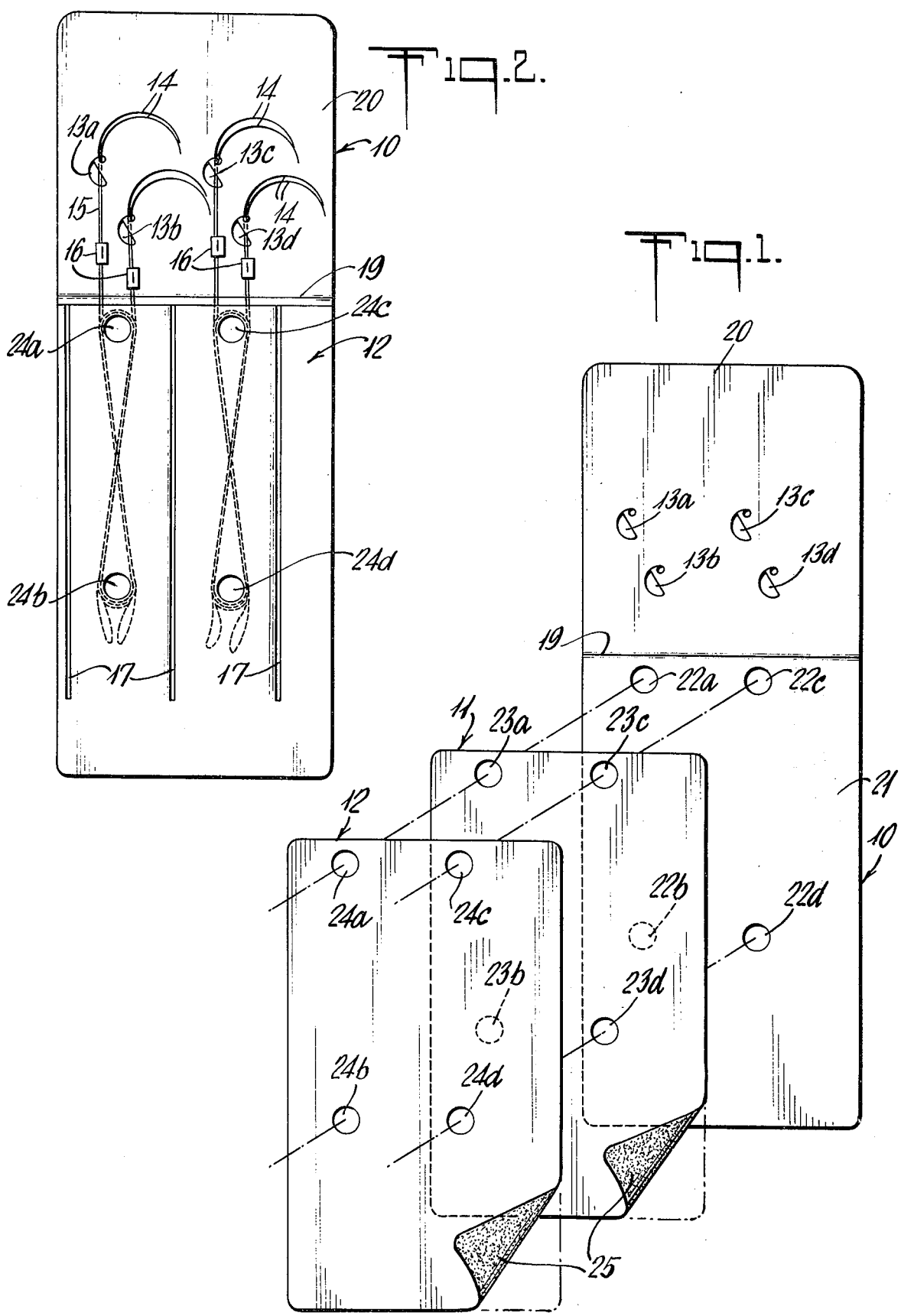

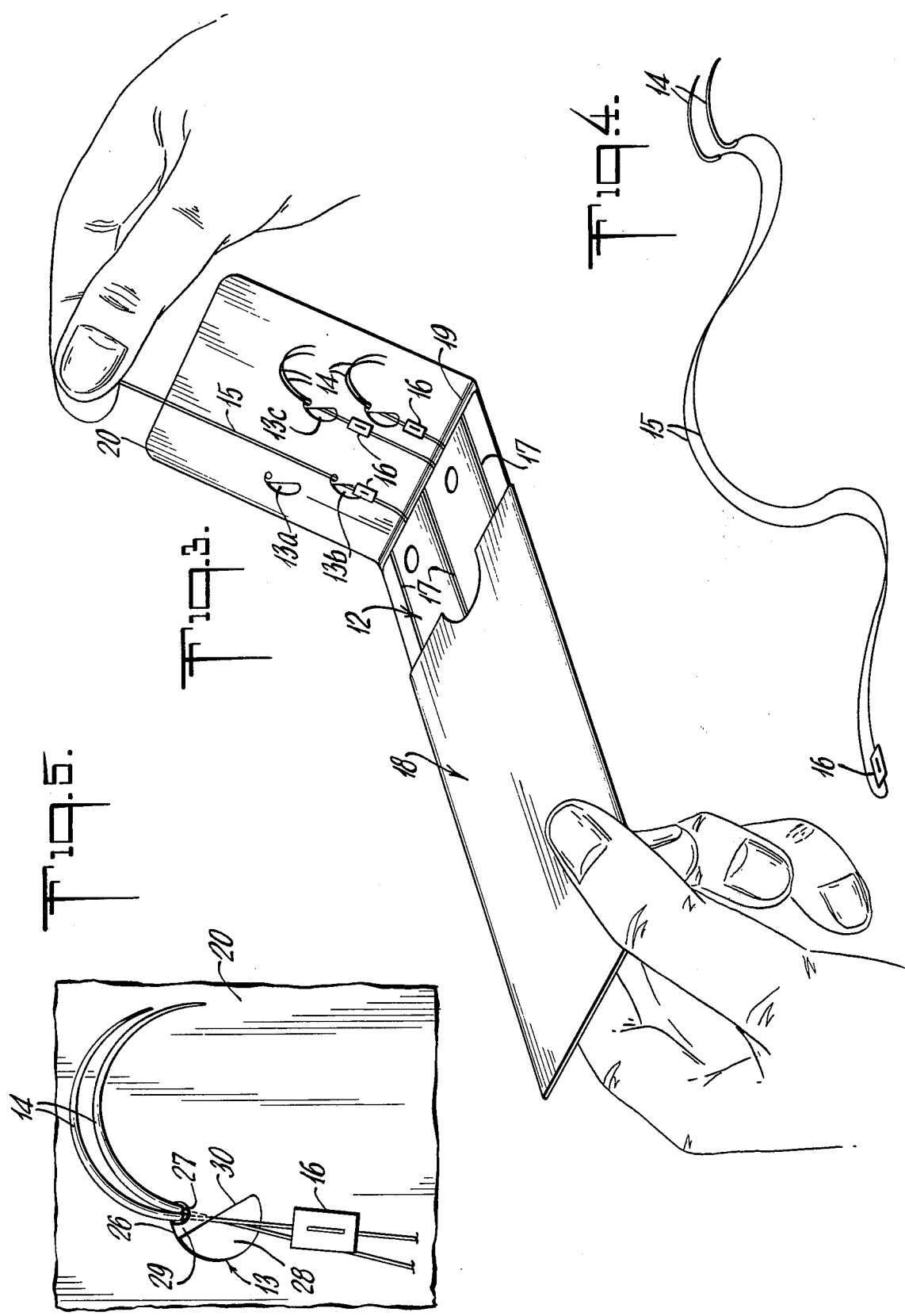

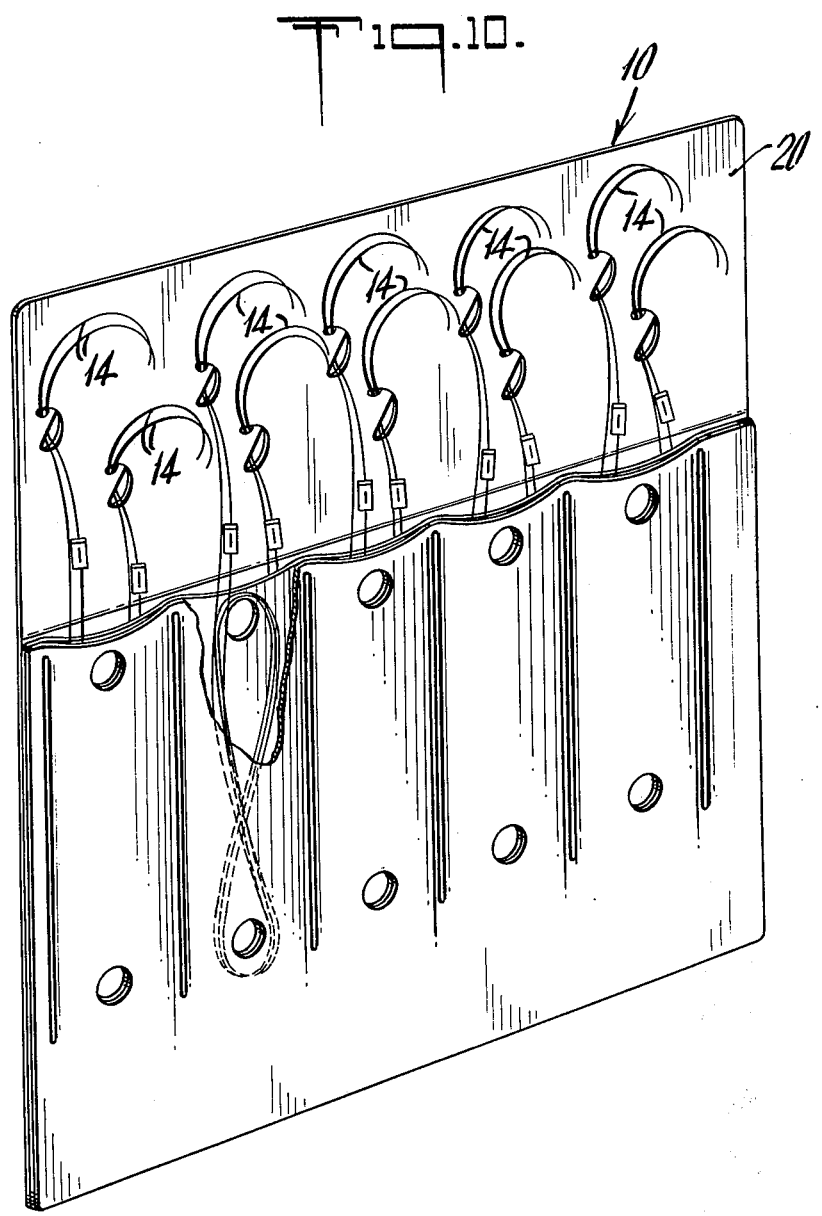

PACKAGE FOR DOUBLE-ARMED SUTURES WITH SELF-CENTERING PLEDGETS

BACKGROUND OF THE INVENTION

1. Field of the Invention

This invention relates to packages for double-armed sutures and more particularly to packages for multiple strands of double-armed sutures wherein each suture is equipped with a pledget which is automatically centered on the suture as the suture is withdrawn from the package.

2. Description of the Prior Art

In the practice of certain surgical procedures involving the suturing of delicate tissue, particularly in cardiovascular operations, it is customary practice to provide the suture with pledget i.e., a cushioning pad, to prevent the suture strand from cutting into the tissue. Practice has been for the surgeon to cut a small piece of felt, fabric or similar material to form the pledge, thread the suture through the pledget and center the pledget on the suture between the needles as required for use.

Double-armed suture have also been made available to the surgeon with pledgets already attached. Although such double-armed sutures have been packaged in both single and multicompartment packages, none of these packages have been equipped with self-centering devices for the pledget, and as a result, it has been necessary for the surgeon to manually center the pledget on the suture after first removing the suture from the package.

Prior art packages for single sutures include, among others, folded suture packages as shown in U.S. Pat. No. 3,444,994, incorporated herein by reference. One preferred package of the present invention comprises an improvement of such a package wherein pledget centering means are provided on a panel extending from the suture compartment. Prior art packages for multistrand double-armed sutures include, among others, those shown in U.S. Pat. Nos. 3,759,376 and 3,857,484, both of which patents are incorporated herein by reference. One preferred package of the present invention incorporates many of the features of these reference packages, but provides as an improvement thereon, integral pledget centering means which provide for automatic centering of the pledget as the suture is withdrawn from the package.

It is accordingly an object of the present invention to provide a new and improved package for double-armed surgical sutures. It is a further object of this invention to provide a package for single or multiple strands of double-armed sutures which are individually equipped with a pledget. It is a yet further object of this invention to provide a package for multiple double-armed sutures wherein pledgets attached to individual sutures near one needle are automatically centered between the needles as each suture is withdrawn from the package. These and other objects will be apparent from the ensuing description and claims.

SUMMARY

A suture package is provided which comprises a double-armed suture in a suture storage compartment with the armed ends of the suture extending out of the compartment. A pledget is affixed to one end of the structure intermediate one needle and the suture storage compartment and pledget centering means are provided intermediate the needle and the pledget. The pledget centering means preferably include a suture strand passageway sized smaller than the pledget so that the suture strand passes easily through the passageway during withdrawal of the suture from the package, but the pledget is restrained at the suture passageway and is slidably displaced along the length of the suture until the suture is fully withdrawn from the package. The sutures with the centered pledget are finally released from the package when the suture is fully withdrawn. Packages for multiple double-armed sutures are provided which hold up to ten or more sutures within adjacent, individual storage compartments.

BRIEF DESCRIPTION OF DRAWINGS

FIG. 1 is an exploded view in perspective of the top, bottom and intermediate panels that form a multiple suture package.

FIG. 2 is a plan view of the suture package of FIG. 1 assembled and loaded with four double-armed sutures and attached pledgets.

FIG. 3 is a perspective view of the suture package of FIG. 2 during the withdrawal of a suture therefrom.

FIG. 4 is a perspective view of a double-armed suture with a pledget centered theron.

FIG. 5 is a plan view of a preferred pledget centering means.

FIG. 10 is a partially sectioned perspective view of a package loaded with ten double-armed sutures and attached pledgets.

DESCRIPTION OF PREFERRED EMBODIMENTS

Figure 6:
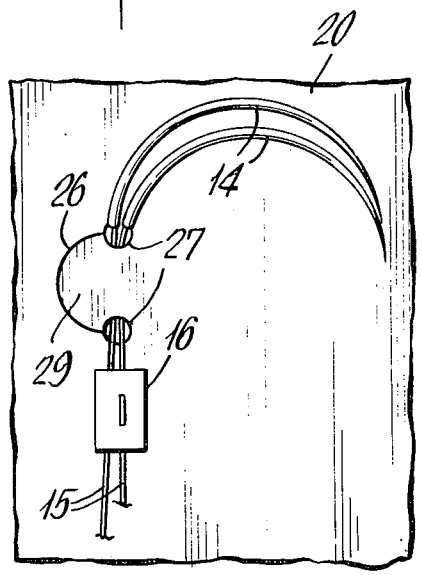
FIG. 6 is a plan view of an alternative pledget centering means.
Figure 7:
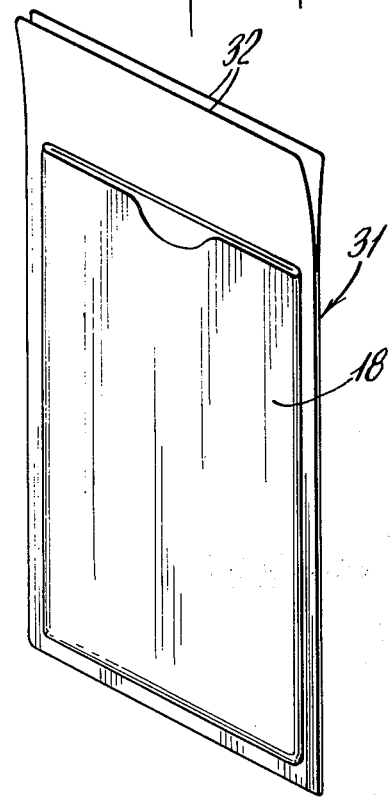
FIG. 7 is a perspective view of a folded suture package of FIG. 2 in a retaining sleeve and hermetically sealed in a sterile outer envelope.

Referring to the drawings, FIG. 1 shows a bottom panel 10, a top panel 12 and an intermediate panel 11 of a three-panel package containing compartments for four suture strands. Bottom panel 10 consists of an upper section 20 and a lower section 21 separated by fold line 19. Upper section 20 is die-cut with four pledget centering means 13a—13d. Lower section 21 is optionally die-cut with four openings 22a—22d which facilitate winding the sutures in the form of a figure eight for packaging as hereinafter described.

Intermediate panel 11 is sized to correspond to the lower section of bottom panel 10 and has four openings 23a—23d corresponding to the four openings 22a—22d in the bottom panel. Intermediate panel 11 is coated on the side adjacent bottom panel 10 with a film 25 of a heat sealing composition, for example, a low density polyethylene or a polyvinylchloride.

Top panel 12 is a duplicate of intermediate panel 11 which is coated with a heat sealing composition on the side adjacent the intermediate panel.

The panels are conveniently constructed of any relatively stiff foldable card-like material including paper, paperboard and plastic and laminates of these with each other, fabric or metal foil. Particularly preferred materials are paperboard such as 5 point to 12 point solid bleached sulfate board or 27 pounds per ream bleached Kraft paper.

The suture packages are assembled using a suture winding jig and heat sealing dies similar to those described in detail in U.S. Pat. No. 3,759,376, and reference should be had to this patent information on the package assembly. For convenience, the method is described briefly as follows. Bottom panel 10 is placed upon a jig having four suture winding pins corresponding to holes 22a—22d in the panel so that when the panel is in position, the winding pins project up through these holes. Both strands of a single, double-armed suture are secured in pledget centering means 13b with the previously affixed pledget approximate to one needle, and the attached suture is wound in a figure eight pattern around the pins projecting through holes 22a and 22b. In a similar manner, the strands of a second suture are secured in pledget centering means 13d and the suture strand is wound around the pins projecting through holes 22c and 22d.

Intermediate panel 11 is now placed on the jig over the previously wound sutures and a third single strand double-armed suture is wound over the pins projecting through holes 23a and 23b, the strands being secured in the pledget centering means 13a. In a like manner a fourth suture is wound around the pins projecting through holes 23a and 23d and the strands are secured in pledget centering means 13c.

Top panel 12 is now placed on the jig over the previously wound sutures and the package is pressed under a sealing die as described in U.S. Pat. No. 3,759,375 to activate the heat sealing film along the edges of the package and along lines between adjacent sutures, thereby forming individual compartments for each suture contained in the package. The pledget on each suture remains outside the suture storage compartment and between the compartment and the pledget centering means.

FIG. 2 illustrates the completed package containing four individually mounted double-arm suture strands with attached pledgets. Heat seal lines 17 bond the panels together and form suture compartments as illustrated. Upper section 20 of bottom panel 10 forms a cover flap which can be folded forward along line 19 over top panel 12 to enclose and protect the needles and reduce the overall size of the package. The folded package may be placed inside an outer sleeve to maintain the package in its folded configuration.

FIG. 3 illustates the use of a suture package of the present invention wherein the package has been partially withdrawn from sleeve 18, cover flap 20 has been opened and a suture is being withdrawn with one hand while the package and sleeve are grasped with the other. Pledget 16 on the suture being withdrawn abuts the suture passageway of the pledget centering means where it is restrained until the suture is fully withdrawn from the suture compartment.

FIG. 4 illustrates a suture after being withdrawn from the package, pledget 16 being centered on suture strand 15 midway between needles 14.

FIG. 5 illustrates a preferred pledget centering means 13 having a generally circular configuration defined by semi-circular opening 28 and arc 26 extending the circumferential boundary of opening 28 beyond said opening and terminating in aperture 27, with opening 28, arc 26 and aperture 27 all defining projection 29 which serves as a suture securing and pledget stop means. Opening 28 and aperture 27 define a suture passageway in the pledget centering means. During withdrawal of the suture from the package, the suture strands pass easily through the passageway while the pledget is restrained by projection 29 and against straight edge 30 of opening 28. When the end of the center loop of the suture strand reaches the pledget, the pledget is urged along edge 30 toward arc 26 until the suture securing strength of projection 29 is overcome and the suture and pledget are released through arc 26.

In FIG. 6, the pledget centering means includes apertures 27 interconnected by arc 26 which in combination with said apertures defines projections 29. Apertures 27 provide a suture passageway through which the suture is easily withdrawn during removal from the package. The small size of aperture 27 provides a pledget stop means to restrain the pledget as the suture is being withdrawn and to slidably displace the pledget along the length of the suture until the suture is fully withdrawn. After the pledget reaches the center loop of the suture, a continued withdrawal force overcomes the restraining force of projection 29 and suture and pledget are released from the package through arc 26.

As will be readily apparent from the figures and description herein, the pledget centering means also function as effective needle mounting means to maintain the needle pairs together for convenient removal from the packages, and to prevent entanglement of adjacent sutures.

The arrangement of sutures within the package may vary considerably, but a preferred arrangement is illustrated in FIG. 2. In particular and with reference to the two sutures on the left hand side of the package, pledget centering means 13a and 13b are slightly offset to either side of a vertical line extending through the center of suture winding pin openings 24a and 24b. The sutures are then wound in opposite directions so that the sutures exit from the storage compartment on opposite sides of the pin openings. Thus offset, the suture strands and the pledgets remain separated for ease of identification and removal.

The two suture strands on the right hand side of the package are wound and oriented in an identical manner to those on the left. The package provides for an extra width of panel to the right of the sutures in order to accommodate the needles which extend to the right of the pledget centering means.

The package illustrated in FIG. 2 may be expanded by adding additional suture compartments and pledget centering means as desired. In this manner packages containing 6, 8, 10 or more sutures are conveniently constructed. In many instances, packages containing the correct number of sutures for a particular surgical procedure can be provided and such packages can, if desired, contain an assortment of suture and needle sizes with each size prominently and individually marked on the cover flap adjacent each pledget centering means.

The suture package may also assume configurations other than the rectangular shape illustrated in FIG. 2. For example, packages comprising five or more adjacent suture compartments may be square or horizontally rectangular. In other variations, the packages may be heat sealed across the bottom as well as along the sides to enclose the suture compartments on three sides. The panels may also be joined by adhesives or mechanical means as an alternative to heat sealing, or the package may be fabricated from a single sheet with attached panels being folded into the desired positions.

The packages are sterilized after assembly by radiation, heat, ethylene oxide or any other convenient and conventional method which is not incompatible with the package or suture materials. Sterile packages are hermetically sealed in an outer envelope overwrap to preserve sterility. A folded suture package and package sleeve sealed in a transparent, peelable overwrap is illustrated in FIG. 6 where overwrap envelope 31 has peel flaps 32 at one end for easy opening and access to the suture folder. The overwrap is heat sealed around the outer edges using conventional techniques to enclose the inner suture package.

The pledgets employed in the preparation of the packages of the present invention may be of any biologically compatible, needle pierceable resilient material and of a variety of sizes. In general, rectangular pads about 3 mm by 6 mm by 1-2 mm thick are satisfactory for most surgical procedures. The pledgets may be fabricated of fabric, felt, or any similar cushioning material. One preferred pledget material is a Teflon impregnated Teflon or polyester felt. The individual pledgets are affixed to the suture by passing one needle and short length of attached suture through the pledget before packaging the suture.

While the foregoing description has been directed to a suture package having dual superimposed suture compartments and a double row of pledget centering means as illustrated in FIG. 2 it will be readily appreciated that similar packages having only a single row of compartments can be fabricated in a like manner utilizing only two panels, e.g., panels 10 and 11 of FIG. 1. In such a package, only a single row of pledget centering means is required in cover flap 20 since there is only a single suture for each compartment position. The package of FIG. 2 may accordingly be reduced in size to provide storage for only one or two suture strands if so desired.

Figure 8:
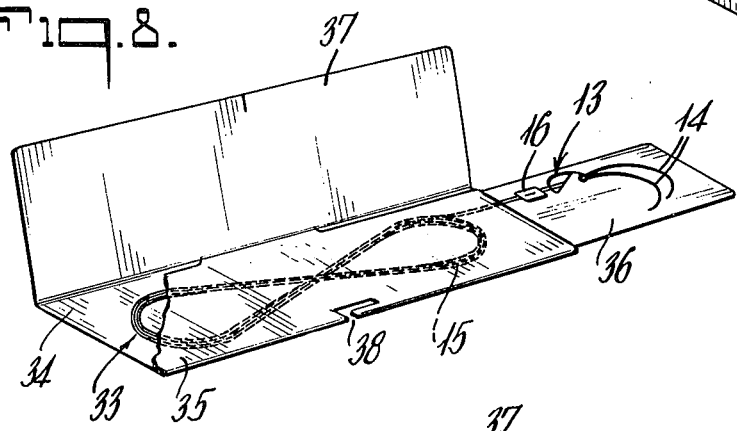
FIG. 8 is a perspective view of a folded package for a single suture, partially unfolded to view the pledget centering means.

While multistrand packages are generally preferred for cardiovascular procedures, sutures equipped with self-centering pledgets may also be provided in individually packaged units. A popular folded package for individual sutures is described in U.S. Pat. No. 3,444,994, and a modification of such a package to include pledget centering means is illustrated in FIG. 8. With particular reference to this Figure, suture 15 is contained within the suture compartment 33 formed by folded panels 34 and 35. Panel 36 extending from the suture compartment contains pledget centering means 13. Panel 36 is adapted to be folded forward over panel 35 and cover panel 37 is folded over panel 36 and interlocked with panels 34 and 35 at locking slot 38 to hold the package in the folded configuration.

The foregoing description has also been directed toward a preferred package wherein the suture strands within the suture compartment are wound in the form of a figure eight. This is a preferred suture configuration which provides for rapid suture packaging and for subsequent withdrawal of the suture from the package with minimal danger of entanglement. There are, however, many permissible variations in the method by which the suture package of the present invention may be constructed. For example, the packages may be formed first and the sutures coiled and inserted into the individual compartments. Alternatively, the suture strands may be inserted into preformed compartments in a random manner although the incidence of entanglement upon removal may be somewhat higher than for a prewound figure eight coil.

Figure 9:
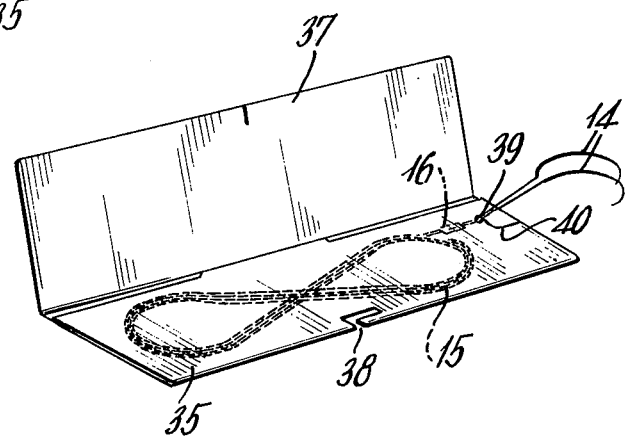
FIG. 9 is a perspective view of a package having pledget centering means included in the wall of the suture compartment.

Packages of the present invention are characterized by providing a suture storage compartment, pledget centering means spaced from said compartment, a double-armed suture contained in said compartment with both armed ends extending therefrom, and a pledget slidably affixed onto the suture strand approximate to one needle and between the pledget centering means and the suture storage compartment. The pledget centering means preferably including a pasageway for the suture and a restraining means for the pledget to permit passage of the suture strand but not the pledget during withdrawal of the suture from the package. The pledget centering means is conveniently provided on a panel extending from the suture compartment although other arrangements are possible such as, for example, including the pledget centering means in the wall of the suture compartment as illustrated in FIG. 9 where the pledget centering means comprises aperature 39 connected to the outer edge of panel 35 by cut 40.

Many other variations in package structure or design which nevertheless utilize the pledget centering features of the packages of the present invention will be apparent to those skilled in the art. The present invention accordingly is not limited by the specific embodiments presented herein.

What is claimed is:

1. A suture package comprising at least two panels and a suture storage compartment between said panels, a suture strand contained within said compartment with both ends of said suture strand extending from the compartment, a needle affixed to each end of said suture strand, a pledget slidably attached to said suture strand adjacent one of said needles, and pledget centering means in one of said panels intermediate said pledget and said needle for centering the pledget on the suture strand as said suture strand is withdrawn from said compartment.

2. A package of claim 1 wherein said pledget centering means are incorporated in a panel extending beyond the suture storage compartment.

3. A package of claim 1 wherein said pledget centering means include a passageway for the suture and restraining means for the pledget.

4. A package of claim 2 wherein said suture passageway is an opening in said panel of said package and said pledget restraining means is a projection across said opening.

5. A package of claim 1 wherein said pledget centering means are incorporated in a panel forming a wall of the suture storage compartment.

6. A package of claim 1 wherein said pledget is a felt of a biologically acceptable material.

7. A package for double-armed sutures comprising at least two panels forming a suture storage compartment having at least one open end,
   a double-armed suture contained in said compartment with both armed ends extending from the open end thereof,
   a pledget slidably affixed to the suture strand adjacent one end of said strand,
   pledget centering means in one of said panels spaced from said suture storage compartment and intermediate said pledget and the end of said suture strand,
   said pledget centering means comprising a passageway for said suture strand and pledget stop means whereby when said suture strand is withdrawn from the package compartment through the suture passageway, the pledget engages the pledget stop means and is slidably displaced along the length of the suture until the suture is completely removed from the package.

8. A package of claim 7 wherein said suture is coiled in the form of a figure eight within said suture storage compartment.

9. A package of claim 7 wherein said pledget centering means comprises a projection defined by a semi-circular opening and an arc extending the circumferential boundary of said opening and terminating in an aperture.

10. A package of claim 7 wherein said pledget centering means comprises a projection defined by two apertures and an interconnecting arc.

11. A multistrand suture package for double-armed sutures comprising a first panel having a bottom edge, a top edge and two side edges, said panel being divided into an upper section and a lower section, a second panel overlying the lower section of said first panel and sealed to said first panel along spaced lines parallel to said side edges to form a plurality of adjacent compartments that are opened at the top edge of said second panel, a suture strand contained within each of said compartments with both ends of said suture strand extending from the open end of said compartment, a needle affixed to each end of said suture strand, a pledget slidably attached to said suture strand adjacent one of said needles, pledget centering means spaced from said suture compartment in said upper section of said first panel, said pledget centering means including a suture strand passageway sized smaller than said pledget whereby when the suture strand is withdrawn from the package compartment through the passageway the pledget is restrained by the passageway and slidably displaced along the length of the suture until the suture is completely removed from the package.

12. A package of claim 11 wherein a film of a heat sealing composition is provided between said first and second panels and said panels are heat sealed along said lines to form a plurality of compartments.

13. A package of claim 12 wherein said heat sealing composition is a low density polyethylene.

14. A package of claim 11 wherein said first and second panels are constructed of a relatively stiff foldable material.

15. A package of claim 11 wherein said material is paperboard.

16. A package of claim 11 wherein the upper section of the first panel is folded forward over the second panel and said folded package is retained in its folded position by a retaining sleeve.

17. A package of claim 16 enclosed in a sterile, hermetically sealed envelope.

18. A package of claim 11 comprising a third panel overlying said second panel and sealed thereto along lines coinciding with the lines of sealing between said first and second panels to form a plurality of adjacent compartments coinciding with the underlying compartments between said first and second panels, and said panels are heat sealed along said lines to form a plurality of said compartments.

19. A package of claim 18 wherein the heat sealing composition is low density polyethylene.

20. A package of claim 18 containing from four to ten suture compartments.

21. A package of claim 18 wherein said third panel is constructed of paperboard.

22. A package of claim 11 wherein said pledget is needle pierceable biologically acceptable material.

23. A package of claim 22 wherein said pledget is a felt pad selected from the group consisting of a polytetrafluoroethylene or polyethylene terephthalate.

* * * * *

UNITED STATES PATENT AND TRADEMARK OFFICE
CERTIFICATE OF CORRECTION

PATENT NO. : 4,034,850
DATED : July 12, 1977
INVENTOR(S) : Harvey B. Mandel et al It is certified that error appears in the above-identified patent and that said Letters Patent are hereby corrected as shown below:

In Column 1, line 67, "of the structure" should read --- of the suture ---.

In Column 3, line 6, "to this patent information" should read --- to this patent for specific information ---.

In Column 3, line 49, "Figure 3 illustates" should read --- Figure 3 illustrates ---.

In Column 5, line 30, "in Figure 2" should read --- in Figures 2 and 10 ---.

In Column 6, line 11, "preferably including a pasageway" should read --- preferably including a passageway ---.

Signed and Sealed this

Thirteenth Day of June 1978

[SEAL]

Attest:

RUTH C. MASON
Attesting Officer

DONALD W. BANNER
Commissioner of Patents and Trademarks